United States Patent
Kim et al.

(10) Patent No.: US 8,735,491 B2
(45) Date of Patent: May 27, 2014

(54) SOLVENT BONDABLE THERMOPLASTIC ELASTOMERS

(75) Inventors: Sehyun Kim, McHenry, IL (US); Wayne Thornton, Whitman, MA (US)

(73) Assignee: PolyOne Corporation, Avon Lake, OH (US)

( * ) Notice: Subject to any disclaimer, the term of this patent is extended or adjusted under 35 U.S.C. 154(b) by 349 days.

(21) Appl. No.: 13/140,013

(22) PCT Filed: Dec. 1, 2009

(86) PCT No.: PCT/US2009/066270
§ 371 (c)(1),
(2), (4) Date: Jun. 15, 2011

(87) PCT Pub. No.: WO2010/074896
PCT Pub. Date: Jul. 1, 2010

(65) Prior Publication Data
US 2011/0251596 A1    Oct. 13, 2011

Related U.S. Application Data

(60) Provisional application No. 61/138,028, filed on Dec. 16, 2008.

(51) Int. Cl.
*C08L 9/06*    (2006.01)
*C08K 5/09*    (2006.01)

(52) U.S. Cl.
USPC ........... 524/525; 524/322; 524/526; 604/533; 156/294

(58) Field of Classification Search
USPC ............ 524/525, 322, 526; 604/533; 156/294
See application file for complete search history.

(56) References Cited

U.S. PATENT DOCUMENTS

| | | | |
|---|---|---|---|
| 6,303,200 B1 | 10/2001 | Woo et al. | |
| 6,815,475 B2 * | 11/2004 | Donald et al. | 524/81 |
| 6,977,105 B1 * | 12/2005 | Fujieda et al. | 428/36.9 |
| 7,250,129 B2 * | 7/2007 | Williams et al. | 264/328.17 |
| 2006/0178485 A1 | 8/2006 | Shimakage et al. | |

* cited by examiner

*Primary Examiner* — Robert D. Harlan
(74) *Attorney, Agent, or Firm* — John H. Hornickel; Michael J. Sambrook

(57) ABSTRACT

An essentially halogen-free, plasticizer-free thermoplastic elastomer compound is disclosed. The compound has from 10-80 weight percent of a hydrogenated styrene butadiene copolymer having a styrene content of less than 20 weight percent; from 20-90 weight percent of a polyolefin; and less than about 3 weight percent of antioxidant. The compound is capable of being solvent bonded or welded to another thermoplastic material using cyclohexanone alone or with methyl ethyl ketone. The compound is especially useful as medical tubing connected to other parts of medical equipment. The bond strength of the compound to the other thermoplastic material is properly determined only after multiple days of bonding.

9 Claims, No Drawings

400
SOLVENT BONDABLE THERMOPLASTIC ELASTOMERS

CLAIM OF PRIORITY

This application claims priority from U.S. Provisional Patent Application Ser. No. 61/138,028 filed on Dec. 16, 2008, which is incorporated by reference.

FIELD OF THE INVENTION

This invention relates to thermoplastic elastomers, polymer compounds which exhibit elasticity while remaining thermoplastic, which are useful in medical products, particularly medical tubing

BACKGROUND OF THE INVENTION

The world of polymers has progressed rapidly to transform material science from wood and metals of the 19$^{th}$ Century to the use of thermoset polymers of the mid-20$^{th}$ Century to the use of thermoplastic polymers of later 20$^{th}$ Century.

Thermoplastic elastomers combine the benefits of elastomeric properties of thermoset polymers, such as vulcanized rubber, with the processing properties of thermoplastic polymers.

Medical tubing is made from a variety of materials, typically sterilized and diameters are small. Glass, metal, plastic, and silicone rubber tubing are used in a variety of medical applications. The material commonly used for medical tubing is plasticized polyvinyl chloride (PVC). The plasticized PVC, however, is considered to be undesirable not only because of the migration of the plasticizer to the surface but also because of halogen-containing compounds are not favored. It is therefore generally of great interest to develop an alternative non-halogen material for the medical tubing to replace the plasticized PVC.

For example, one manufacturer of elastomeric material, Kraton Polymers U.S. LLC, has brought two hydrogenated styrene-butadiene copolymers (SBC) to the market, which have been identified as useful for medical applications, namely: grades MD6932 and MD6945. Kraton Polymers U.S. LLC has also filed a patent application, WO 2005/095511 A1 (Maris et al.), which identifies hydrogenated styrenic block copolymer compositions which are useful for overmolding in medical tubing applications.

SUMMARY OF THE INVENTION

However, neither the market nor the manufacturer of these leading styrene block copolymer resins has recognized the need for a compound which can be used in medical tubing in situations where durable connection is needed.

More specifically, makers of medical tubing who desire a non-halogenated compound for their tubing also need a type of tubing which makes secure connection to other items such as connectors, made from other plastic materials such as PVC, polycarbonate (PC) or polymethylmethacrylate (PMMA).

Even more specifically, makers of intravenous tubing sets which deliver medicine fluid to the patient need a compound for the tubing which can be bonded or welded to connectors which are capable of connection to other parts of the injection device, such as the fluid reservoir, the pump, the pressure pillow, and other tubing.

For the connection of the tubing to the connectors, solvent bonding or welding is a preferred technique because of ease of operation, strength and durability of the bond or weld. Also it is a relatively inexpensive process which survives later treatment of the medical products, such as sterilization. Because most of the components of the injection device or set are designed to be single-use for medical reasons and therefore must be conveniently disposable, manufacturing cost of the tubing, connectors and other single-use items is particularly important. Typical solvents that have been used for PVC are cyclohexanone or its mixture with methyl ethyl ketone.

Therefore, a need exists in the art for a compound that can be used as medical tubing, which is non-halogenated and also solvent-bondable to PVC, PC, or PMMA.

It has been found that the compound needed for medical tubing requires extrudability, solvent bondability to the connectors, resistance to kinking, no odor, gamma radiation stability, chemical resistance to drugs flowing through the tubing, low extractables from the tubing, low leachables from the tubing, and non-tackiness after sterilization. For transfer of medicine fluid, clarity of the tube is also strongly preferred for monitoring the flow of the critical medicinal fluid.

The present invention solves these problems and results in a thermoplastic elastomer compound which can be used as medical tubing specifically for the purpose of solvent bonding or welding to connectors for use with other medical equipment.

One aspect of the invention is an essentially halogen-free, plasticizer-free thermoplastic elastomer compound, comprising (a) from 10-80 weight percent of a hydrogenated styrene butadiene copolymer having a styrene content of less than 20 weight percent; (b) from 20-90 weight percent of a polyolefin; and (c) less than about 3 weight percent of antioxidant, wherein the compound is capable of being solvent bonded or welded to another thermoplastic material using cyclohexanone alone or with methyl ethyl ketone.

Another aspect of the invention is medical tube set comprising (a) a connector made from a thermoplastic selected from the group consisting of polymethylmethacrylate, polyvinyl chloride, and polycarbonate and (b) medical tubing made from the thermoplastic elastomer compound described above, wherein the connector and the tubing are solvent bonded or welded together using cyclohexanone alone or with methyl ethyl ketone.

Another aspect of the invention is a method of connecting the connector described above to a tubing described above comprising the steps of (a) applying a solvent comprising cyclohexanone to exterior of the tubing and (b) contacting the tubing to the connector for sufficient time to permit the solvent to form a bond between the tubing and the connector.

Features of the invention will become apparent with reference to the following embodiments.

EMBODIMENTS OF THE INVENTION

Hydrogenated Styrene Butadiene Copolymer

Kraton Polymers U.S. LLC sells branded Kraton G hydrogenated styrene butadiene copolymers, also known as styrene-ethylene/butylene-styrene (SEBS). Of the many grades of Kraton branded SEBS polymers, it has been found that a Kraton branded SEBS polymer resin which has a styrene content of less than 20% is useful in the present invention because the low styrene content is needed to achieve the Shore A hardness values needed for medical tubing, particularly if no plasticizer were to be present in the compound. Desirably, the styrene content is less than 18% and preferably less than 15%. Of those candidates, use of Kraton MD6945 SEBS is preferred. It is known that Kraton MD6945 SEBS has a percentage styrene content of about 11-14 percent, a glass transition temperature of −38° C., and a Shore A hardness of 35.

It was unexpectedly found that a SEBS having low styrene content can be solvent bonded or welded to medical device connectors. This unexpectedness arose from a willingness to test for bonding strength for as long as three days. Others do not wait so long before conducting bonding strength tests.

By comparison other hydrogenated SBC (styrene block copolymer) grades are unsuitable for this invention because their styrene content is greater than 20 weight percent. Examples of those grades include Kraton G 1650 SEBS and Kraton G 1651 SEBS from Kraton Polymers US LLC and Septon 8004 and Septon 4033 from Kuraray America Inc. and the like produced by various hydrogenated SBC manufacturers.

Polyolefin

For the thermoplastic elastomer compound, a thermoplastic polymer is needed to be blended with the preferred elastomeric SEBS described above. Polyolefins are preferred thermoplastic polymers for thermoplastic elastomer compounds because of cost and performance.

Of the candidate polyolefins, polypropylenes are preferred. The polypropylene can be a homopolymer or a copolymer.

There are several multi-national and national companies producing polyolefins. Among them is Ineos, which makes acceptable polypropylene for purposes of this invention.

Optional Additives

The thermoplastic elastomer compounds of the present invention can include conventional plastics additives in an amount that is sufficient to obtain a desired processing or performance property for the compound. The amount should not be wasteful of the additive nor detrimental to the processing or performance of the compound. Those skilled in the art of thermoplastics compounding, without undue experimentation but with reference to such treatises as *Plastics Additives Database* (2004) from Plastics Design Library (www.williamandrew.com), can select from many different types of additives for inclusion into the compounds of the present invention.

Non-limiting examples of optional additives include adhesion promoters; biocides (antibacterials, fungicides, and mildewcides), anti-fogging agents; anti-static agents; bonding, blowing and foaming agents; dispersants; fillers and extenders; smoke suppressants; expandable char formers; impact modifiers; initiators; lubricants; micas; pigments, colorants and dyes; plasticizers; processing aids; other polymers; release agents; silanes, titanates and zirconates; slip and antiblocking agents; stabilizers; stearates; ultraviolet light absorbers; viscosity regulators; waxes; and combinations of them.

However, it must be noted that the rigorous requirement of an odor-free product precludes the use of bonding promoters or other additives which might otherwise assist in solvent bonding or welding but detract from the performance of the compound as medical tubing.

Therefore, it is desirable for the essentially halogen-free thermoplastic compound to consist essentially of (a) from 10-80 weight percent of a hydrogenated styrene butadiene copolymer having a styrene content of less than 20 weight percent; (b) from 20-90 weight percent of a polyolefin; and (c) less than about 3 weight percent of antioxidant.

Table 1 shows the acceptable, desirable, and preferable ranges of ingredients for the thermoplastic elastomer compound of the present invention.

TABLE 1

Ranges of Ingredients

| Ingredient (Wt. Percent) | | | |
|---|---|---|---|
| | Acceptable | Desirable | Preferable |
| Hydrogenated Styrene Butadiene Copolymer having <20% styrene content | 10-80% | 20-70% | 20-60% |
| Polyolefin | 20-90% | 30-80% | 40-80% |
| Anti-oxidant | 0-3% | 0-2% | 0-1% |
| Other Additives | 0-15% | 0-10% | 0-5% |

Processing

The preparation of compounds of the present invention is uncomplicated once the proper ingredients have been selected. The compound of the present can be made in batch or continuous operations.

Mixing in a continuous process typically occurs in an extruder that is elevated to a temperature that is sufficient to melt the polymer matrix with addition of all additives at the feed-throat, or by injection or side-feeders downstream. Extruder speeds can range from about 50 to about 500 revolutions per minute (rpm), and preferably from about 400 rpm. Typically, the output from the extruder is pelletized for later extrusion or molding into polymeric articles.

Subsequent extrusion or molding techniques are well known to those skilled in the art of thermoplastics polymer engineering. Without undue experimentation but with such references as "Extrusion, The Definitive Processing Guide and Handbook"; "Handbook of Molded Part Shrinkage and Warpage"; "Specialized Molding Techniques"; "Rotational Molding Technology"; and "Handbook of Mold, Tool and Die Repair Welding", all published by Plastics Design Library (www.williamandrew.com), one can make articles of any conceivable shape and appearance using compounds of the present invention.

EXAMPLES

Table 2 shows sources of ingredients for the examples.

TABLE 2

| Ingredient | Commercial Source |
|---|---|
| Kraton MD6945 SEBS (13% styrene content) | Kraton Polymers U.S. LLC, Houston, Texas |
| R01C-01 polypropylene copolymer with clarifier (2 MFR) | Ineos, League City, Texas |
| Profax PD 702NW polypropylene (35 MFR) | LyondellBasell, Houston, TX |
| Kraton G 1642 SEBS (21% styrene content) | Kraton Polymers U.S. LLC, Houston, Texas |
| Kraton G 1650 SEBS (30% styrene content) | Kraton Polymers U.S. LLC, Houston, Texas |
| Kraton G 1651 SEBS (30% styrene content) | Kraton Polymers U.S. LLC, Houston, Texas |
| Kraton G 1652 SEBS (30% styrene content) | Kraton Polymers U.S. LLC, Houston, Texas |
| Hybrar 7311 SEBS (12% styrene content) | Kuraray America Inc., Pasadena, Texas |
| Kraton FG1901X SEBS (bonding promoter) | Kraton Polymers U.S. LLC, Houston, Texas |
| SEPTON 8006 SEBS (35% styrene content) | Kuraray America Inc., Pasadena, Texas |
| SEPTON 4033 hydrogenated poly(styrene-b-isoprene/butadiene-b-styrene) (SEEPS) | Kuraray America Inc., Pasadena, Texas |
| Plexiglas VM100 PMMA (bonding promoter) | Altuglas International, Philadelphia, PA |

TABLE 2-continued

| Ingredient | Commercial Source |
|---|---|
| Mineral Oil | Commodity Suppliers |
| D-040-W6 polypropylene | Sunoco Chemicals Philadelphia, PA |
| Regalite R1125 fully hydrogenated thermoplastic resin (bonding promoter) | Eastman Chemicals, Kingsport, TN |
| Erucamide lubricant | Aakash Chemicals & Dye Stuffs Inc, Glendale Hts, IL |
| Irganox 1010 antioxidant | Ciba Specialty Chemicals, Tarrytown, NY |
| Ethanox 330 antioxidant | Ciba Specialty Chemicals, Tarrytown, NY |
| Irgafos 168 antioxidant | Ciba Specialty Chemicals, Tarrytown, NY |

All ingredients for each Example and each Comparison Example were fed into the throat of a twin screw extruder having a mixing speed of 400 rpm and a temperature of 360° F. in Zone 1, 380° F. in Zone 2, 400° F. in Zone 3, 430° F. in Zone 4, 400° F. in Zones 5-8 and Die. After compounding, pellets were formed and either molded into tensile testing bars or plaques or extruded into tubing having an outer diameter of 0.145-0.168 inches and an inner diameter of 0.100-0.118 inches, except as otherwise noted in the Tables below.

Table 3 shows the test methods employed and the results obtained. Standard physical performance testing was performed using standard tensile test bars, cutouts from a plaque molded from the compound. Haze testing was performed using a 3.17 mm thick plaque molded from the compound. In addition, a solvent bonding test was performed to test the adhesion of solvent bonding or welding of tubing made from the compound with standard issue medical connectors made of polymethylmethacrylate (PMMA).

The solvent bonding test involved dipping the tubing extruded from the compound into the solvent identified in the Tables and then attaching the tubing into a hole in the connector made of PMMA. At specific intervals thereafter, a sample of the tubing and connector was placed in an Instron Tensile Testing apparatus and subjected to tension at the rate of 20 inches/minute. The force required to pull the tubing from the connector was measured in pounds to assess the bond strength or adhesion of the tubing to the connector. The maximum time tested was 3 days, which is a good prediction for the maximum bond strength which can be achieved if the bond is allowed to cure for as much as 7-10 days.

It is a feature of the invention that it has been discovered that conventional bond strength testing for solvent bonded or welded interfaces between thermoplastic elastomers and other thermoplastics should not be limited to only one day or a fraction thereof. The present invention relies on the unexpected discovery that it takes days for a solvent bond to achieve full bond strength between a SEBS TPE and another plastic material.

In other words, others have not pursued the use thermoplastic elastomers as medical tubing in part because the solvent bonding for PVC achieves maximum bond strength in a matter of a few hours, whereas it takes days for the thermoplastic elastomer to achieve that maximum bond strength. As seen below in Table 3, it is important to recognize that the use of a low styrene content SEBS and the patience to allow the solvent to fully evaporate combine to recognize the unexpected result that one can use a SEBS TPE as medical tubing, without plasticizer, and achieve an acceptable bond between the tubing and a plastic connector.

Table 3 shows the recipes of the Example and Comparison Example compounds, respectively, and the Properties measured for those compounds.

Examples 2 and 4 were tubing having an interior diameter of 0.104 inches. Example 8 had 0.040 inches interior diameter. All other Examples and Comparison Examples had tubing with an interior diameter of 0.118 inches.

TABLE 3

| | Part 1 | | | | | | |
|---|---|---|---|---|---|---|---|
| | 1 | 2 | 3 | 4 | 5 | 6 | 7 |
| | Formulations | | | | | | |
| Kraton MD6945 | 22 | 22 | 60 | 60 | 66 | 71 | 78 |
| R01C-01 | 78 | 78 | 40 | 40 | 34 | 29 | 22 |
| Kraton 1650 | | | | | | | |
| Kraton 1652 | | | | | | | |
| Kraton 1651 | | | | | | | |
| Kraton FG1901X | | | | | | | |
| SEPTON 8006 (SEBS) | | | | | | | |
| SEPTON 4033 (SEEPS) | | | | | | | |
| Plexglas VM100 | | | | | | | |
| mineral oil | | | | | | | |
| D-040-W6 | | | | | | | |
| Regalite R1125 | | | | | | | |
| Erucamide | | | | | | | |
| Irganox 1010 | | | | | | | |
| Ethanox 330 | 0.1 | 0.1 | 0.1 | 0.1 | 0.1 | 0.1 | 0.1 |
| Irgafos 168 | 0.1 | 0.1 | 0.1 | 0.1 | 0.1 | 0.1 | 0.1 |
| | Properties | | | | | | |
| Shore A Hardness (ASTM D2240, 10s delay) | 95 | 95 | 86 | 86 | 80 | 72 | 66 |
| Specific Gravity (ASTM D792) | 0.89 | 0.89 | 0.88 | 0.88 | 0.88 | 0.89 | 0.88 |
| Tensile Strength, psi (ASTM D412, Die C) | 2263 | 2463 | 1321 | 1321 | 1360 | 960 | 1167 |
| Elongation, % (ASTM D412, Die C) | 573 | 573 | 397 | 397 | 618 | 539 | 483 |

TABLE 3-continued

Solvent Bonding Tests
A = Cyclohexanone; B = Tetrahydrofuran; and C = 15/85 Mixture of Methyl Ethyl Ketone/Cyclohexanone

| | | | | |
|---|---|---|---|---|
| Solvent Bonding Test at 1 Hour (lbs.) | | | | |
| Solvent Bonding Test at 1 Hour (lbs.) | 9.970 A | 9.970 A | 7.260 A | 7.260 A |
| Solvent Bonding Test at 8 Hours (lbs.) | | | 10.150 A | |
| Solvent Bonding Test at 19 Hours (lbs.) | 10.760 A | 10.170 A | 7.170 A | 7.170 A |
| Solvent Bonding Test at 72 Hours (lbs.) | | | 8.820 A | |
| Haze (ASTM D1003) | 49 | 60 | | 61 |

Part 2

| | 8 | A | B | C | D | E |
|---|---|---|---|---|---|---|
| Formulations | | | | | | |
| Kraton MD6945 | 78 | | | | | |
| R01C-01 | 22 | 17 | | | | |
| Kraton 1650 | | 83 | 11.5 | | | |
| Kraton 1652 | | | | 83.1 | | |
| Kraton 1651 | | | 23 | | 32.2 | |
| Kraton FG1901X | | | 3.8 | | | |
| SEPTON 8006 (SEBS) | | | | | | 27.5 |
| SEPTON 4033 (SEEPS) | | | | | | 7.6 |
| Plexglas VM100 | | | 15.3 | | | 9.5 |
| mineral oil | | | 45.9 | 16.6 | 25.7 | 29.4 |
| D-040-W6 | | | | | 22.5 | 25.6 |
| Regalite R1125 | | | | | 19.3 | |
| Erucamide | | | 0.25 | | | |
| Irganox 1010 | | | 0.1 | | 0.1 | |
| Ethanox 330 | 0.1 | 0.1 | | 0.14 | 0.14 | 0.19 |
| Irgafos 168 | 0.1 | 0.1 | 0.15 | 0.11 | | 0.19 |
| Properties | | | | | | |
| Shore A Hardness (ASTM D2240, 10s delay) | 66 | 82 | 47 | 60 | 72 | 85 |
| Specific Gravity (ASTM D792) | 0.88 | 0.9 | 0.91 | 0.89 | 0.91 | 0.9 |
| Tensile Strength, psi (ASTM D412, Die C) | 1167 | 2072 | 478 | 917 | 1377 | 1560 |
| Elongation, % (ASTM D412, Die C) | 483 | 365 | 430 | 652 | 688 | 620 |
| Solvent Bonding Tests A = Cyclohexanone; B = Tetrahydrofuran; and C = 15/85 Mixture of Methyl Ethyl Ketone/Cyclohexanone | | | | | | |
| Solvent Bonding Test at 1 Hour (lbs.) | | 4.7 A | 1.900 B | 4.300 A | 5.200 C* | |
| Solvent Bonding Test at 1 Hour (lbs.) | | | | | | 7.930 A |
| Solvent Bonding Test at 8 Hours (lbs.) | 5.360 A | | | | | |
| Solvent Bonding Test at 19 Hours (lbs.) | | | | | | 8.260 A |
| Solvent Bonding Test at 72 Hours (lbs.) | | 5.5 A | 6.500 A | | 6.100 C* | |
| Haze (ASTM D1003) | | | | | | |

*Methyl Ethyl Ketone evaporates in approximately two hours.

Examples 1-8 all have similar Shore A hardness, specific gravity, tensile strength, and elongation values to Comparison Example A, demonstrating that medical tubing made from a low styrene content SEBS was not detrimental to the physical properties of a thermoplastic elastomer compound. The variations in amounts of the SEBS and the polypropylene show to one skilled in the art the range of possible physical properties of the compound as used for medical tubing.

Comparison Examples B, D, and E are unsatisfactory for medical tubing because the bonding promoters contribute unacceptable odor to the compound.

Comparison Examples D and E are thermoplastic elastomer compounds, but they do not use a low styrene content SEBS as the elastomer ingredient. The solvent bonding test results of Comparative Example D is inferior to Examples 1-4.

All of Comparison Examples B-E contain mineral oil, an undesirable plasticizer. The solvent bonding test results of Comparison Examples B-D are inferior to Examples 1-4. Comparison Examples B and D have unacceptably low bond strength even with the use of odorous bond promoters. Comparison Example C has an unacceptably low bond strength using a oil extended formulation and no bond promoter additives.

Comparison Example E is seen to have an acceptable bond strength, well above 5 pounds of breakage force required by government regulation. But Comparison Example E uses odorous bond promoters, making it a failure for medical tubing uses.

Examples 1-4 achieve all of the objectives of the invention without relying on odorous bond promoters. Examples 1-4 all have bond strength well above 5 pounds of breakage force and exceed in most cases a preferred commercial value of 8 pounds of breakage force.

The difference between Examples 1 and 3 from Examples 2 and 4 shows that the size of tubes does introduce some variability in bond strength, but all are well above 5 pounds of breakage force.

The difference between Examples 1 and 2 from Examples 3 and 4 shows that a wide variation in formulation ratio of SEBS to polyolefin is possible while still achieving all objectives of the present invention.

The use of a hydrogenated styrene butadiene copolymer having a styrene content of less than 20 weight percent is critical to the performance of the compounds of the present invention. While it may appear suitable that Comparative Example A has comparable solvent bond strength to Example 8, there are other important physical properties to be considered: surface appearance, clarity, and whether the tube recovers after kinking or clamping.

Examples 9-10 and Comparative Examples F-G

Table 4 shows how the type of hydrogenated styrene butadiene copolymer affects the performance of tubes made from those compounds. All the ingredients were pre-mixed using a Henschel mixer and then compounded using a co-rotating twin screw extruder. The extrudate was pelletized with a Gala underwater pelletizer. To determine the mechanical properties of the compounds, the plaques (12.7 cm×15.2 cm×0.32 cm) were molded with an injection molding machine using the following temperature profile and processing conditions:

Temperature: 227/227/204/182° C.

Processing conditions: 15.17 MPa, 120 rpm, 0.5 sec, 6.2 MPa/6.2 MPa, 5/5/25 hold time/pack time/cool time, in seconds.

The following physical properties were tested according to the following standard methods: Specific Gravity: ASTM D792; Hardness (Shore A): ASTM D2240, 10s delay; Capillary Rheology: determined at 200° C.; and Tensile properties: ASTM D412, Die C. Specialized test methods were:

Tube extrusion: To evaluate solvent bondability, the pellets were extruded to a tube of 4.16 mm (±0.63 mm) outer and 2.79-2.95 mm (±0.63 mm) inner diameter, using a Brabender extruder at 190° C. Using an appropriate tubing die, the RPM of the extruder was adjusted to produce a tube with a desirable outer diameter for the bond test.

Solvent Bonding Test: For a tube-connector assembly, the tube was cut to a length of 10.16 cm. One end of the tube was dipped into cyclohexanone, a common solvent that has been used in the IV tubing industry for a long time, and inserted into the connector made of PMMA. After 1, 24 or 72 hrs, the connector-tube assembly was loaded on Instron and the tube was pulled out from the connector and the force or the energy required to pull out was recorded. The pull-out force was determined as a maximum force to pull-out the tube while the energy required to pull out was determined by the area under the curve. In general, a minimum of 5 lbf (22 Newtons) of pull-out force is required for IV tubing.

Kink of Tube Test: The tube was tested for kinks by folding the tube to form a 2.54 cm diameter circle. The tube that formed a kink was not acceptable for medical intravenous tubing.

TABLE 4

| Example | 9 | 10 | F | G |
|---|---|---|---|---|
| MD6945 | 65.7 | | | |
| 7311 | | 62.4 | | |
| G1650 | | | 65.7 | |
| G1652 | | | | 59.9 |
| R01C-01 | 34.1 | 37.4 | 34.2 | 39.9 |
| AO (antioxidant, Ethanox 330 and Irgafos 168) | 0.2 | 0.2 | 0.1 | 0.2 |
| Rheology @200° C. | | | | |
| Viscosity @ 67023/sec | 10.3 | 9.8 | 8.7 | 17.9 |
| Viscosity @ 11170/sec | 35.7 | 35 | 33.8 | 71.7 |
| Viscosity @ 1340.5/sec | 171 | 160 | 172.6 | 337 |
| Viscosity @ 223.41/sec | 618 | 550 | 603.6 | 1286 |
| Viscosity @ 67.023/sec | 1360 | 1261 | 1416.3 | 2944 |
| Molded Plaque | | | | |
| Hardness (Shore A) | 80 | 84 | 88 | 90 |
| 50% Modulus (psi) | 476 | 625 | 709 | 1340 |
| Extruded Tube | | | | |
| surface | smooth | smooth | smooth | smooth |
| Clarity of tube | clear | clear | translucent | translucent |
| Kink | N | N | Y | Y |
| Pullout force (lbf) - 1 hr | — | — | 16 | 23 |
| Pullout energy (lbf · in) - 1 hr. | — | — | 18.2 | 29 |
| Pullout force (lbf) - 24 hrs. | 6 | 7 | 14 | 21 |
| Pullout energy (lbf · in) - 24 hrs. | 20.1 | 13.2 | 11.1 | 19.5 |
| Total % Styrene | 8.5 | 7.5 | 19.7 | 17.4 |
| η(R01C-01)/η(Rubber) at 223/sec (η: viscosity) | 0.62 | 0.69 | <<0.27 | 0.27 |

The difference in tube properties between Examples 9-10 and Comparative Examples F-G is directly attributable to the percentage styrene content in the compound. Kinking of tubes and translucency are unacceptable for medical grade tubing, even if solvent bonding results are acceptable.

Examples 11-18

Additional embodiments of the invention resulted from Examples 11-16. The compounds were made and tested in the same manner as for Examples 9 and 10. Table 5 shows the recipes and results. Erucamide wax was added in these Examples to assist in the restoration of the tube circumference after clamping pressure was removed.

TABLE 5

| Example | 11 | 12 | 13 | 14 | 15 | 16 | 17 | 18 |
|---|---|---|---|---|---|---|---|---|
| MD6945 | 59.7 | 59.9 | 59.7 | 59.7 | 50.4 | 50.4 | 65.6 | 50.4 |
| G1642H | — | — | — | — | 12.6 | 12.6 | — | 12.6 |
| R01C-01 | 39.8 | 31.9 | 24.9 | 19.9 | 36.5 | 18.3 | 19.9 | 36.5 |
| Profax PD702NW | — | 8.0 | 14.9 | 19.9 | — | 18.3 | 13.9 | — |
| Wax-Erucamide | 0.2 | 0 | 0.2 | 0.2 | 0.22 | 0.22 | 0.25 | 0.22 |
| AO (antioxidant, Ethanox 330 anf Irgafos 168) | 0.3 | 0.2 | 0.3 | 0.3 | 0.32 | 0.32 | 0.3 | 0.32 |
| Rheology @ 200° C. | | | | | | | | |
| Viscosity @ 67023/sec | 10.4 | 10.2 | 9.8 | 9.9 | 10.8 | 9.7 | 9.9 | 12.0 |
| Viscosity @ 11170/sec | 37.0 | 35.8 | 34.1 | 33.4 | 39.2 | 36.0 | 35.7 | 46.7 |
| Viscosity @ 1340.5/sec | 165 | 166 | 159 | 160 | 190 | 175 | 170 | 218 |
| Viscosity @ 223.41/sec | 598 | 597 | 564 | 581 | 714 | 640 | 609 | 802 |
| Viscosity @ 67.023/sec | 1255 | 1196 | 1094 | 1179 | 1546 | 1292 | 1383 | 1688 |
| Molded plaque | | | | | | | | |
| Hardness Shore A: | 83.5 | 84.2 | 83.9 | 81.9 | 80.2 | 80.9 | 80 | 83 |
| Specific Gravity: | 0.88 | 0.88 | 0.88 | 0.88 | 0.88 | 0.88 | — | — |
| 50% Modulus (psi): | 784 | 586 | 744 | 632 | 592 | 581 | 515 | 658 |
| Tensile Strength (psi): | 1748 | 1463 | 1789 | 1689 | 1475 | 1608 | 1489.47 | 1429.9 |
| Tensile Elongation (%): | 471 | 473 | 533 | 656 | 533 | 565 | 492.3 | 411.30 |
| Extruded tube | | | | | | | | |
| surface | smooth | smooth | smooth | smooth | smooth | smooth | smooth | smooth |
| clarity | clear | clear | clear | clear | clear | clear | clear | clear |
| Kink | N | N | N | N | N | N | N | N |
| Pullout force (lbf)-1 hr | 10 | 11.5 | 10.7 | 9.3 | 9.9 | 8 | — | — |
| Pullout energy (lbf. in)-1 hr | 36.9 | 71.2 | 39.6 | 46.8 | 49.5 | 17.3 | — | — |
| Pullout force (lbf)-24 hrs | 11.5 | 8.8 | 10.9 | 9.1 | 8.5 | 8.2 | — | — |
| Pullout energy (lbf. in)-24 hrs | 48.5 | 34.5 | 38.2 | 20.4 | 32.3 | 23.2 | — | — |
| Total % styrene | 7.8 | 7.8 | 7.8 | 7.8 | 9.2 | 9.2 | | |

Examples 11-18 demonstrate that all the formulations processed well to the tube, with the hardness and the tensile modulus of the compounds being slightly varied depending on the type of rubber and polypropylene. The pullout force depends on the hardness and/or the modulus of the compound. The pullout energy appears to depend on the type of polypropylene employed in the compound, such that the higher the melt flow of poly, the lower the pullout energy. The presence of wax does not affect the solvent bondability of the tube but does improve clamping recovery intervals.

The tubes from these formulations of Examples 11-18 are clear, smooth, and do not kink.

The discovery that one needs to test for bond strength over an interval of at least two days and preferably longer, in combination with the use of low styrene content SEBS makes this invention unexpectedly beneficial to the life-saving market of medical tubing.

The invention is not limited to the above embodiments. The claims follow.

What is claimed is:

1. A medical tube set comprising (a) a connector made from a thermoplastic selected from the group consisting of polymethylmethacrylate, polyvinyl chloride, and polycarbonate and (b) medical tubing made from an essentially halogen-free, plasticizer-free thermoplastic elastomer compound, comprising:
   (i) from 10-80 weight percent of a hydrogenated styrene butadiene copolymer having a styrene content of less than 20 weight percent;
   (ii) from 20-90 weight percent of a polyolefin; and
   (iii) less than about 3 weight percent of antioxidant;
wherein the connector and the tubing are solvent bonded or welded together using cyclohexanone alone or with methyl ethyl ketone.

2. A method of connecting a connector made from a thermoplastic selected from the group consisting of polymethylmethacrylate, polyvinyl chloride, and polycarbonate to a tubing made of an essentially halogen-free, plasticizer-free thermoplastic elastomer compound comprising: (i) from 10-80 weight percent of a hydrogenated styrene butadiene copolymer having a styrene content of less than 20 weight percent; (ii) from 20-90 weight percent of a polyolefin; and (iii) less than about 3 weight percent of antioxidant; said method comprising the steps of: (a) applying a solvent comprising cyclohexanone to exterior of the tubing and (b) contacting the tubing to the connector for sufficient time to permit the solvent to form a bond between the tubing and the connector.

3. The method of claim 2, wherein the sufficient time is at least two days.

4. A method of connecting the connector made from a thermoplastic selected from the group consisting of polymethylmethacrylate, polyvinyl chloride, and polycarbonate to a tubing made of an essentially halogen-free, plasticizer-free thermoplastic elastomer compound consisting essentially of: (i) from 10-80 weight percent of a hydrogenated styrene butadiene copolymer having a styrene content of less than 20 weight percent; (ii) from 20-90 weight percent of a polyolefin; and (iii) less than about 3 weight percent of antioxidant; said method comprising the steps of (a) applying a solvent comprising cyclohexanone to exterior of the tubing and (b) contacting the tubing to the connector for sufficient time to permit the solvent to form a bond between the tubing and the connector.

5. The method of claim 4, wherein the sufficient time is at least two days.

6. The medical tube set of claim 1, wherein the thermoplastic elastomer compound further comprises erucamide wax.

7. The medical tube set of claim 1, wherein the styrene content of the thermoplastic elastomer compound ranges from about 7 to about 13 percent.

8. The medical tube set of claim 1, wherein the thermoplastic elastomer compound further comprises a second hydrogenated styrene butadiene copolymer.

9. The medical tube set of claim 1, wherein the thermoplastic elastomer compound further comprises a second polyolefin.

\* \* \* \* \*